US 11,353,403 B2

(12) United States Patent
Norriss

(10) Patent No.: US 11,353,403 B2
(45) Date of Patent: Jun. 7, 2022

(54) VIAL CONTENTS INSPECTION AND MATERIAL IDENTIFICATION METHOD AND APPARATUS

(71) Applicant: Genentech, Inc., South San Francisco, CA (US)

(72) Inventor: Andrew David Norriss, Portland, OR (US)

(73) Assignee: Genentech, Inc., South San Francisco, CA (US)

( * ) Notice: Subject to any disclaimer, the term of this patent is extended or adjusted under 35 U.S.C. 154(b) by 116 days.

(21) Appl. No.: 16/696,974

(22) Filed: Nov. 26, 2019

(65) Prior Publication Data
US 2020/0173929 A1    Jun. 4, 2020

Related U.S. Application Data

(60) Provisional application No. 62/835,970, filed on Apr. 18, 2019, provisional application No. 62/773,955, filed on Nov. 30, 2018.

(51) Int. Cl.
*G01N 21/71* (2006.01)
*G01N 21/94* (2006.01)
*G01N 33/15* (2006.01)

(52) U.S. Cl.
CPC .......... *G01N 21/718* (2013.01); *G01N 21/94* (2013.01); *G01N 33/15* (2013.01); *G01N 2201/13* (2013.01)

(58) Field of Classification Search
CPC ...... G01N 21/718; G01N 21/94; G01N 33/15; G01N 2201/13; G01N 21/9027
See application file for complete search history.

(56) References Cited

U.S. PATENT DOCUMENTS

| | | |
|---|---|---|
| 3,751,172 A | 8/1973 | Seitz et al. |
| 4,063,823 A | 12/1977 | Grat |
| 4,417,662 A | 11/1983 | Nicholson et al. |
| 5,141,110 A | 8/1992 | Trischan et al. |
| 5,444,539 A | 8/1995 | van der Grift |
| 5,606,129 A | 2/1997 | Lehmann |
| 5,719,679 A | 2/1998 | Shimizu et al. |
| 5,940,176 A | 8/1999 | Knapp |

(Continued)

FOREIGN PATENT DOCUMENTS

WO    WO2016/137789 A1    9/2016

OTHER PUBLICATIONS

"Lyophilization of Liposomal Formulations: Still Necessary, Still Challenging", Franze et al., Pharmaceutics 2018, 10, 139. (Year: 2018).*

(Continued)

*Primary Examiner* — Mohamed K Amara
(74) *Attorney, Agent, or Firm* — Shay Glenn LLP

(57) ABSTRACT

A method of inspecting and performing material identification of a contaminant found in a vial may include identifying the presence of the contaminant in a lyophilized medicine within the vial, detaching a portion of the vial to create an enlarged opening in the vial, removing substantially an entire cake of lyophilized medicine through the enlarged opening, and analyzing the contaminant using an atomic emissions spectroscopy (AES) technique such as laser-induced breakdown spectroscopy (LIBS). Systems, fixtures and devices associated with the method are also disclosed.

22 Claims, 14 Drawing Sheets

(56) References Cited

U.S. PATENT DOCUMENTS

| | | | |
|---|---|---|---|
| 6,064,479 A | 5/2000 | Knapp | |
| 6,473,169 B1 | 10/2002 | Dawley et al. | |
| 7,626,158 B2 | 12/2009 | Diehr et al. | |
| 9,176,071 B2 | 11/2015 | Weil et al. | |
| 9,415,015 B2* | 8/2016 | Jacobi | A61K 45/06 |
| 2009/0153838 A1 | 6/2009 | Vugts et al. | |
| 2014/0177932 A1* | 6/2014 | Milne | G01N 21/8851 382/128 |
| 2017/0283299 A1 | 10/2017 | Bookbinder et al. | |
| 2019/0233320 A1* | 8/2019 | Nicholas | C03B 33/06 |

OTHER PUBLICATIONS

Coles et al.; U.S. Appl. No. 16/696,945 entitled "Vial inspection method and apparatus," filed Nov. 26, 2019.

Lewen et al.; The use of atomic spectroscopy in the pharmaceutical industry for the determination of trace elements in pharmaceuticals; Journals of Pharmaceutical and Biochemical Analysis; 55(4); pp. 653-661; Jun. 1, 2011.

Chen et al.; Two-step procedure fortrace element analysis in food via calibration-free laser-induced breakdown spectroscopy; Spectrochimica Acta Part B: Atomic Spectroscopy; vol. 150; pp. 77-85; Oct. 22, 2018.

St. Onge et al.; Quantitative analysis of pharmaceutical products by laser-induced breakdown spectroscopy; Spectrochimica Acta Part B: Atomic Spectroscopy; 57(7); pp. 1131-1140; Jul. 1, 2002.

\* cited by examiner

VIAL CONTENTS INSPECTION AND MATERIAL IDENTIFICATION METHOD AND APPARATUS

CROSS REFERENCE TO RELATED APPLICATIONS

This application claims the benefit of U.S. Provisional Application Ser. No. 62/773,955 filed Nov. 30, 2018, and U.S. Provisional Application Ser. No. 62/835,970 filed Apr. 18, 2109, each of which are herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

The present disclosure relates to inspection systems, in particular to systems and methods for inspecting the contents of glass vials and identifying materials found therein.

BACKGROUND

Various products such as medicines are provided in glass vials. Medicines are often provided in a lyophilized form. Lyophilization is a freeze-drying process that removes water from a product after it is frozen and placed under a vacuum. Some of the typical pharmaceutical products that undergo lyophilization include bulk pharmaceutical/biopharmaceutical ingredients (chemical or biologics found in nature), protein, collagen, peptide, oligonucleotide, chemical API, enzymes, and monoclonal antibodies. If the bulk drug ingredients are not stable in liquid or frozen form, lyophilization is highly advantageous. This can be due to chemical reactions, degradation, aggregation, biological growth, heat sensitivity, etc. Lyophilization enables longer shelf life, often as long as two-five years and makes it much easier to transport the product. In addition, products can be stored at room temperature.

During the manufacture of pharmaceuticals, vial filling and/or lyophilization processes, contaminate particles may inadvertently be introduced into the vial. These particles need to be analyzed in order to determine their source and prevent similar particles from being introduced into later vials being processed. Typical analysis of the contaminate particles involves reconstitution and filtering of lyophilized product in order to isolate a particulate for analysis. This traditional process has the potential of introducing additional foreign particulate, can result in the loss of the particulate being analyzed, and can be time consuming.

What is needed and not provided by the prior art are improved systems and methods to inspect contaminants found in lyophilized medicines within glass vials.

SUMMARY OF THE DISCLOSURE

The present disclosure relates to systems and methods for inspecting/identifying the contents of a glass vial. The present disclosure provides new ways of accessing lyophilized cakes using the principals of glass fracture mechanics, and shows how Atomic Emissions Spectroscopy (AES)/Laser-induced breakdown spectroscopy (LIBS) can be used to identify a certain category of suspected particulate in a lyophilized protein cake.

According to aspects of the disclosure, a method of inspecting and performing material identification of a contaminant found in a vial containing a cake of lyophilized medicine is provided. In some embodiments, the method includes identifying the presence of a contaminant in the lyophilized medicine, detaching a base or other portion of the vial to create an enlarged opening in the vial, removing substantially an entire cake of lyophilized medicine through the enlarged opening, and analyzing the contaminant using an atomic emissions spectroscopy (AES) technique.

In some embodiments of the above method, the AES technique comprises laser-induced breakdown spectroscopy (LIBS). In some embodiments, the contaminant remains on the lyophilized cake while being analyzed by LIBS equipment. In some embodiments, the contaminant is a speck and may comprise stainless steel.

In some embodiments, the step of detaching the portion of the vial includes scoring a heel of the vial. A fixture may be used to position the vial relative to an awl. In some embodiments, the fixture allows the vial to be rotated relative to the awl. The vial has a central longitudinal axis and the fixture may hold the vial such that its axis is at a non-perpendicular angle relative to the awl. In some embodiments, the non-perpendicular angle is about 75 degrees. The step of detaching the portion of the vial may include applying a force to the base of the vial at a diameter that is smaller than a diameter of the base. In some embodiments, the force is applied to the base at a diameter that is about half of the diameter of the base. A force gauge may be used to measure the force being applied to the base. In some embodiments, the force gauge is mounted on a press configured to move the force gauge relative to the vial. The step of detaching the portion of the vial may include tapping a heel of the vial.

In some embodiments, the method further includes confirming the occurrence of the contaminant at least three times. The step of analyzing the contaminant may include comparing a signal associated with the contaminant with a signal associated with a sample taken from a component of pharmaceutical processing equipment. In some embodiments, the contaminant signal is compared to a library comprising at least ten samples taken from different components of pharmaceutical processing equipment.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Before the present invention is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "the component" includes reference to one or more components, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Figure 1:
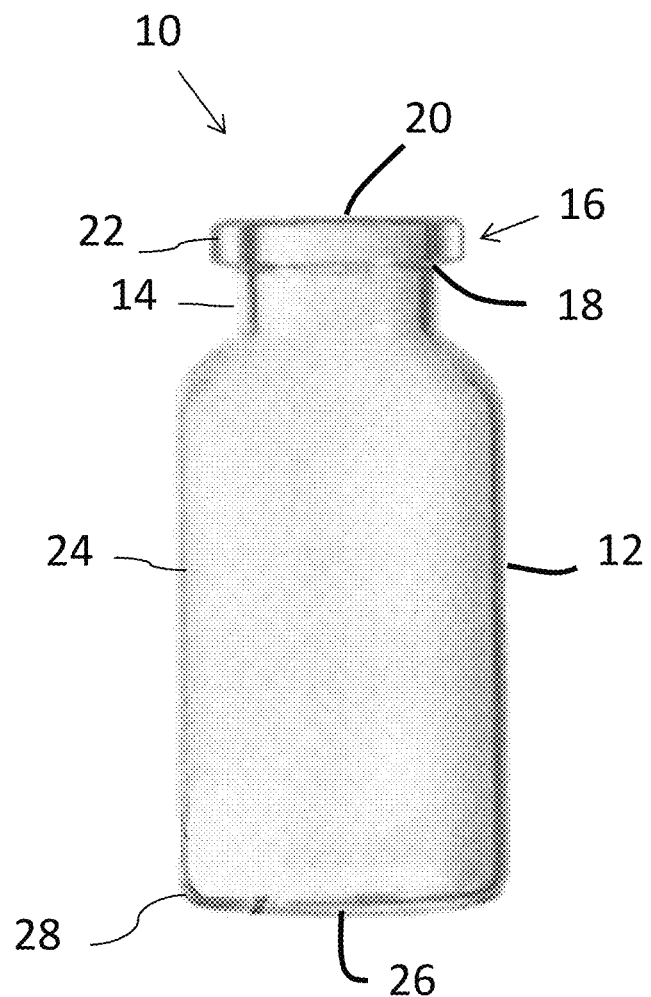
FIG. 1 is a side view showing a prior art glass vial, the contents of which are to be analyzed.

Referring to FIG. 1, an exemplary glass medicine vial 10 is shown. Medicine vials are manufactured in various shapes and sizes, but typically have a main portion 12 of constant diameter, a neck 14 having a reduced diameter, and a lip 16 or flange located around the vial opening (not shown) at the top of the neck 14. Flange 16 may have a diameter greater than that of neck 14 to provide an undercut portion or collar 18. After vial 10 is filled with medicine, the top may be sealed with a septum material or crown 20 held in place by a metal band, crimp, seal or finish 22 that covers a portion of crown 20, flange 16 and collar 18. Crown 20 may be pierced with a hypodermic needle to reconstitute lyophilized medicine and to withdraw medicine from the vial into a syringe. The curved edge located at the bottom of main portion 12 as the sidewalls 24 transition into the bottom surface or base 26 of the vial may be referred to as the heel 28 of the vial.

Lensing (which is identifiable by the base of the vial detached from the body) may occur in the glass vial. This can occur unintentionally when a defect such as a fissure forms on the heel of the vial. A fissure can be created by thermal and/or mechanical stresses placed on the vial, such as when the vial is being filled with medicine and during manufacturing and logistical processes consistent with the manufacturing environment. Further stresses can cause the defect to propagate around the entire heel of the vial, causing the base 26 to detach from the main body 12 of vial 10 (and form a separate piece of glass shaped like a lens.) Lensing is generally regarded as something to be avoided in glass medicine vials, and steps are typically taken at various stages of design, manufacture and distribution to ensure it does not occur. However, according to aspects of the present disclosure, lensing can be actively employed to aid in the inspection and identification of the vial contents.

Figure 2:
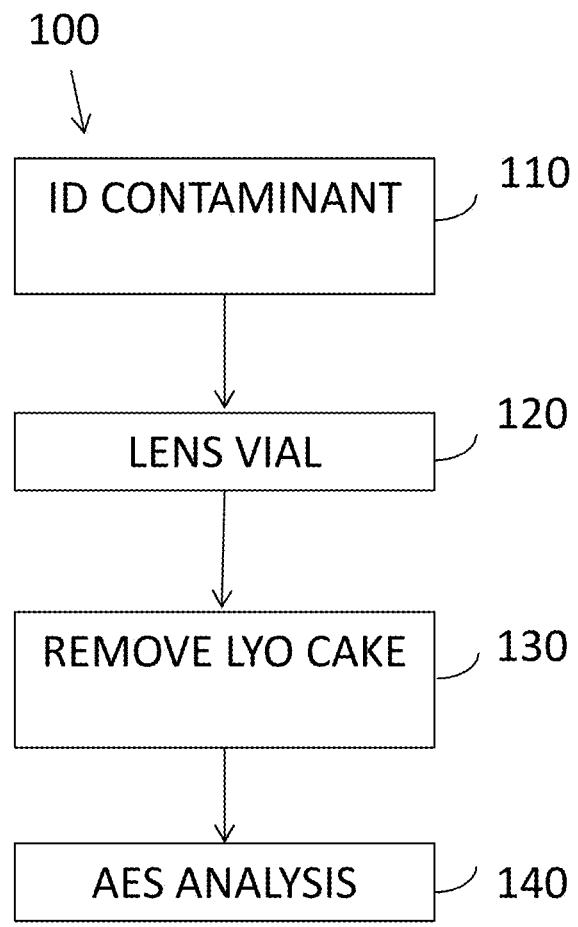
FIG. 2 is diagram showing the steps of an exemplary embodiment of a vial contents inspection and analyzation method performed according to aspects of the present disclosure.

Referring to FIG. 2, an exemplary embodiment of a vial contents inspection and identification method 100 performed according to aspects of the present disclosure will be described. In this exemplary embodiment, inspection and identification method 100 includes the steps of:

110—identifying the presence of a contaminant in a lyophilized medicine;

120—lensing or detaching a base or other portion of the vial to create an enlarged opening in the vial;

130—removing substantially an entire cake of lyophilized medicine through the enlarged opening; and 140—analyzing the contaminant using an atomic emissions spectroscopy (AES) technique.

Each of these steps will be described in detail in the following discussion.

Figures 3, 4:
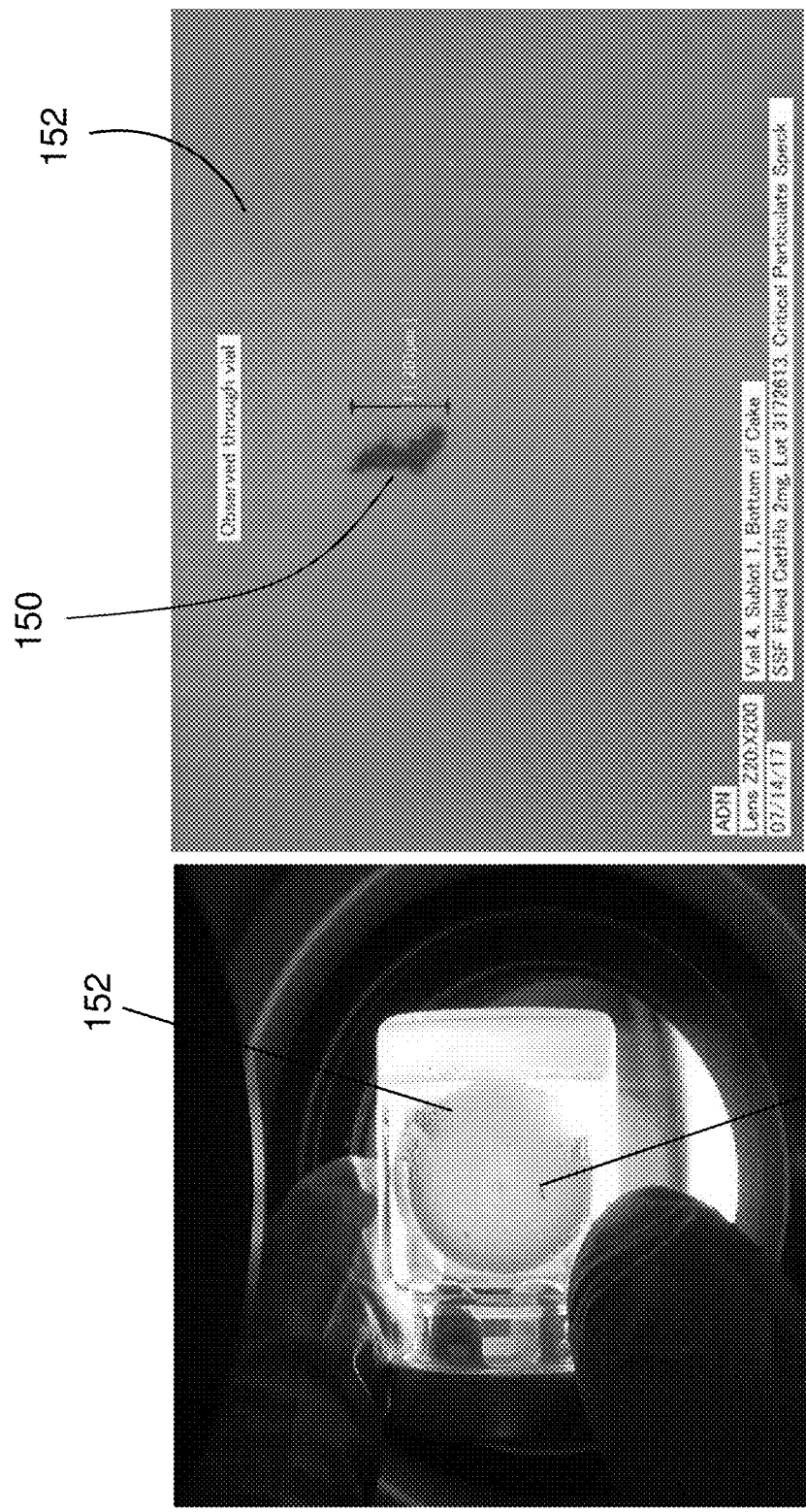
FIG. 3 is a side view of a vial whose contents are being illuminated.
FIG. 4 is an enlarged view showing a contaminant particle in the vial of FIG. 3.

Referring to FIGS. 3 and 4, step 110 of the exemplary inspection method 100, identifying the presence of a contaminant in a lyophilized medicine, will be described. Contaminants may be classified into three categories: speck, fiber, glass. A fiber may be defined as a particulate having a large aspect ratio, such as 4:1, and one that typically floats or has a neutral buoyancy. A glass contaminant typically is a particulate made of clear glass. A speck can be defined as any particulate that is not a fiber or glass. A speck specifically includes metal and rubber particulates. The following discussion focuses on but is not necessarily limited to particulates that are classified as specks.

One or more vials containing a suspected contaminant may be culled from a larger batch of vials during an inspection process of the vials. This may occur soon after the vials have been filled and lyophilized. The tops of the vials may also be sealed at this point.

In some implementations of exemplary inspection method 100, confirmation that one or more specks or other contaminant occurs is performed at least three times. First, existence of a speck on a lyophilized cake within the vial is confirmed before the vial is lensed. Second, confirmation of the speck is performed after the vial is lensed. Third, confirmation of the speck on a spectrometer is performed. These at least three confirmations may be performed by the same or different technicians/analysts. An exemplary first confirmation of a speck is shown in FIGS. 3 and 4. Light may be transmitted through vial 10 from behind to highlight an opaque particle 150 on top of a lyophilized (lyo) cake 152, as shown in FIG. 3. FIG. 4 shows particle 150 with top lighting on lyo cake 152 as seen with a digital microscope with calibrated measurement capabilities (observed through vial 10.) In this example, particle 150 has an elongated shape and measures 201 micrometers across. During this first confirmation of particle 150, images such as FIGS. 3 and 4 may be taken, and the morphology, color, location and other characteristics of particle 150 may be recorded for a subsequent analyst. If the existence of a particle cannot be confirmed at this point, inquiry may be made with personnel associated with the previous inspection to reassess or explain why it was culled. Exemplary second and third confirmations of particle 150 will be subsequently described in more detail with the discussion of later steps of method 100.

Figure 5:
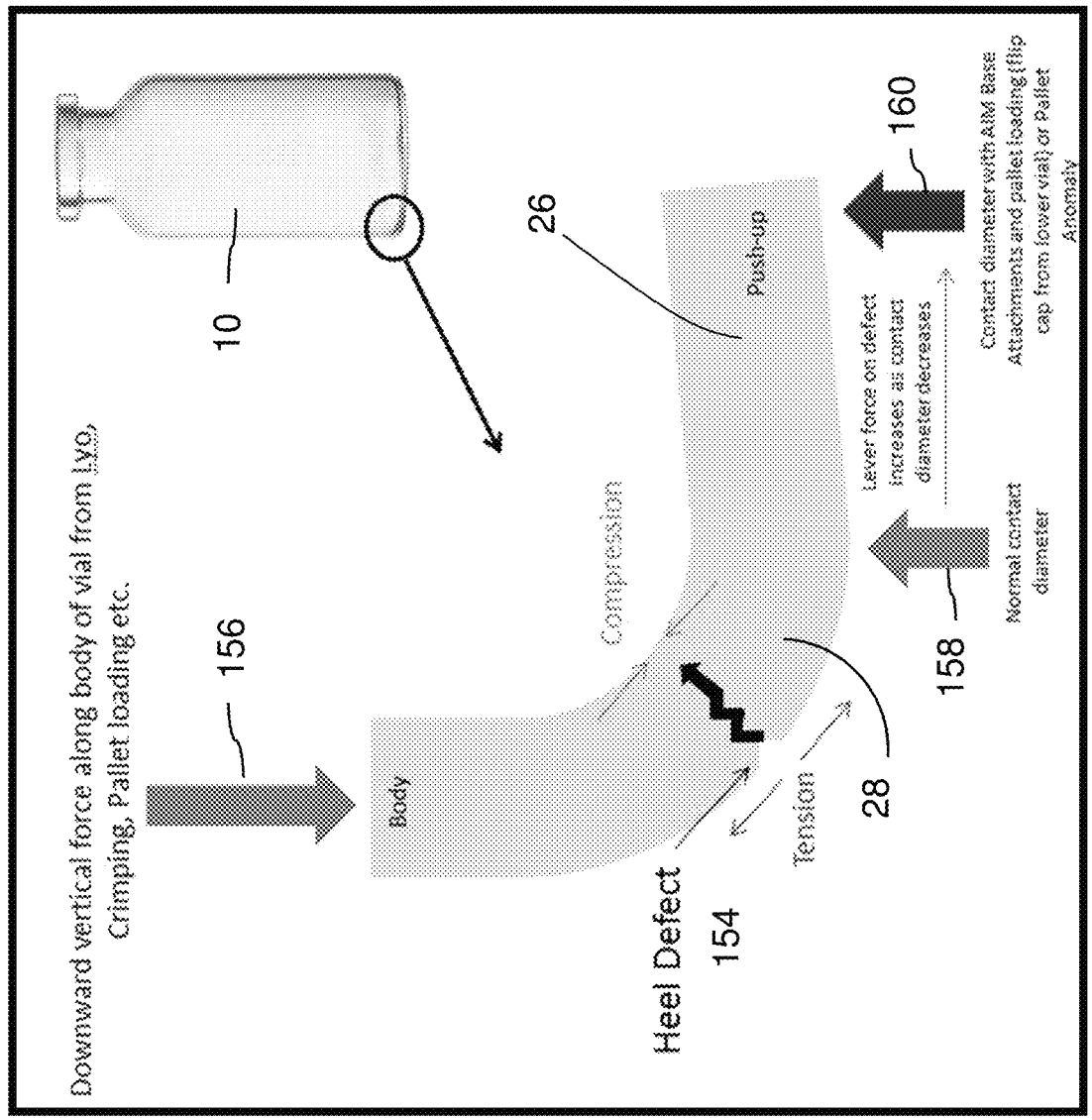
FIG. 5 is a side view of a vial, and an inset view showing an enlarged portion of the vial.

Referring to FIGS. 5-11, step 120 of the exemplary inspection method 100, lensing or detaching a base or other portion of the vial to create an enlarged opening in the vial, will be described. Referring first to FIG. 5, the mechanics of fracturing the base 26 of vial 10 will be described. If a defect such as a fissure 154 is introduced into heel 28 (either unintentionally or intentionally), this can create a starting point for a crack that will extend around the entire heel 28 if certain stresses are applied to vial 10. When vial 10 sits on a flat surface and receives a downward vertical force 156 from above such as from filling, lyophilizing or crimping equipment or from pallet loading, etc., an upward counteracting force 158 is applied at a normal contact diameter as shown. Because this force occurs at a relatively small distance from heel 28, it may be enough to create a defect 154 but typically is not enough to cause it to propagate. If, however, the same upward force is applied near the center of base 26 at a small contact diameter (force 160 shown in FIG. 5), this creates a longer lever or moment about fissure 154 and can cause it to propagate transversely through heel 28 and laterally around its circumference. During normal operations, this can be unintentionally caused by the same equipment that may have caused the initial fissure 154. However, according to aspects of the present disclosure, the initial fissure 154 and an upward loading force 160 at a small contact diameter may be intentionally applied to vial 10 under controlled conditions for lensing vial 10 in order to remove lyo cake from it substantially intact.

Figure 7:
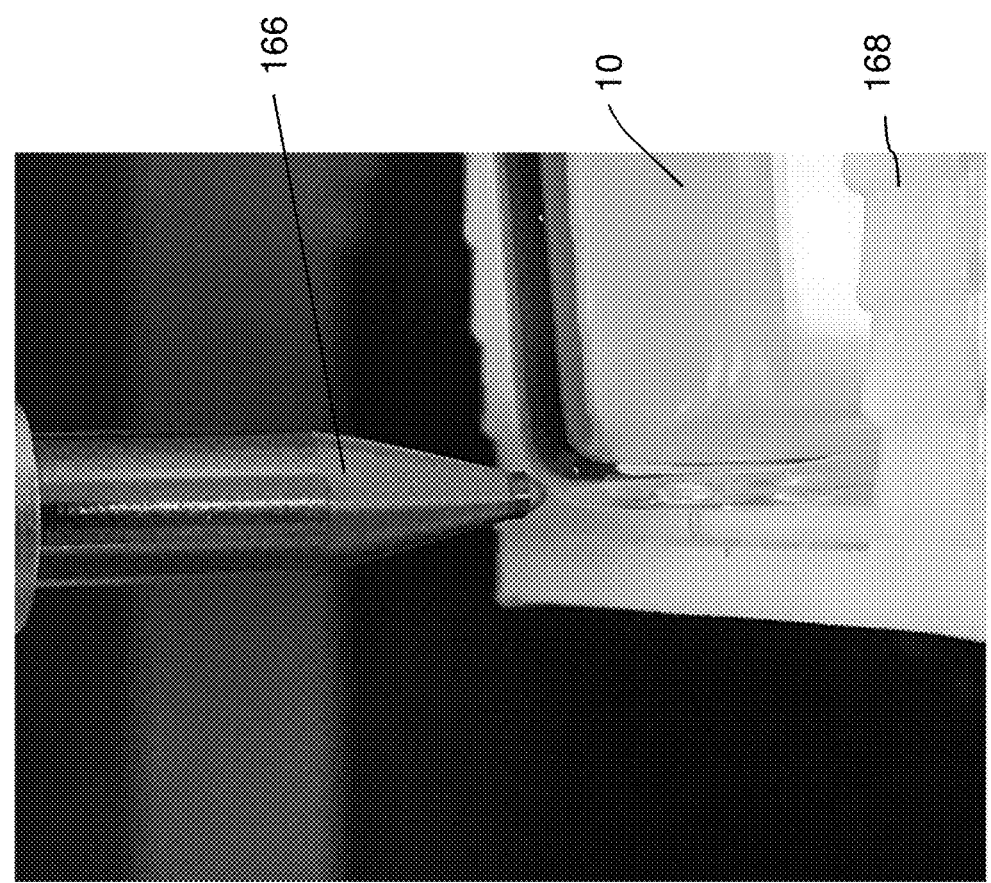
FIG. 7 is an enlarged front view showing a portion of the vial and apparatus of FIG. 7.
Figure 6:
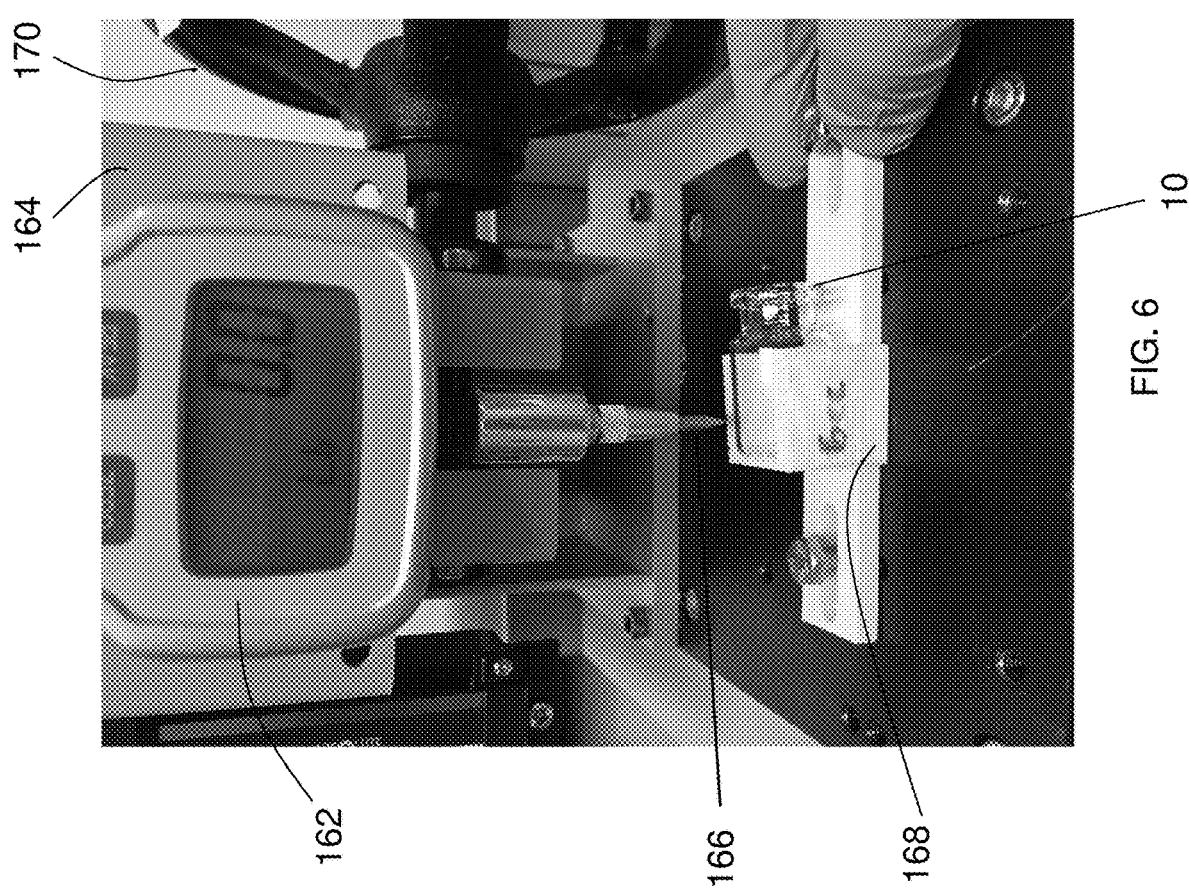
FIG. 6 is a front view of vial scoring apparatus.

Referring to FIGS. 6 and 7, equipment and fixtures for introducing a fissure into heel 28 of vial 10 are shown. In some implementations of inspection method 100, a force gauge 162 (such as a model FGV-200XY digital force gauge sold by NIDEC-SHIMPO Corporation) may be mounted on a vertical press 164. A carbide-tipped awl 166 may be mounted in the force gauge 162, as shown. A fixture 168 may be provided to securely hold one or more vials below awl 166. In some embodiments, fixture 168 is made from a thermoplastic, and may be fabricated with an additive manufacturing process such as 3D printing. In some embodiments, fixture 168 holds vial 10 at an angle, such as about 15 degrees above horizontal. In this orientation, a central longitudinal axis of vial 10 forms an angle of about 75 degrees relative to awl 166. In some embodiments, this angle is between about 85 degrees and about 60 degrees. Separate fixtures may be provided for each vial size and shape, or a V-shaped fixture may be used to hold a variety of vial types. Crank or wheel 170 of press 164, shown in FIG. 6, is turned to lower awl 166 onto heel 28 of vial 10, as shown in FIG. 7. In some embodiments, a predetermined downward force of awl 166 onto vial 10, as read out on force gauge 162, is maintained as vial 10 is rotated within fixture 168 to create a score line or other surface defect on heel 28. In some embodiments, this surface defect is created continuously around the circumference of base 26.

Figure 8:
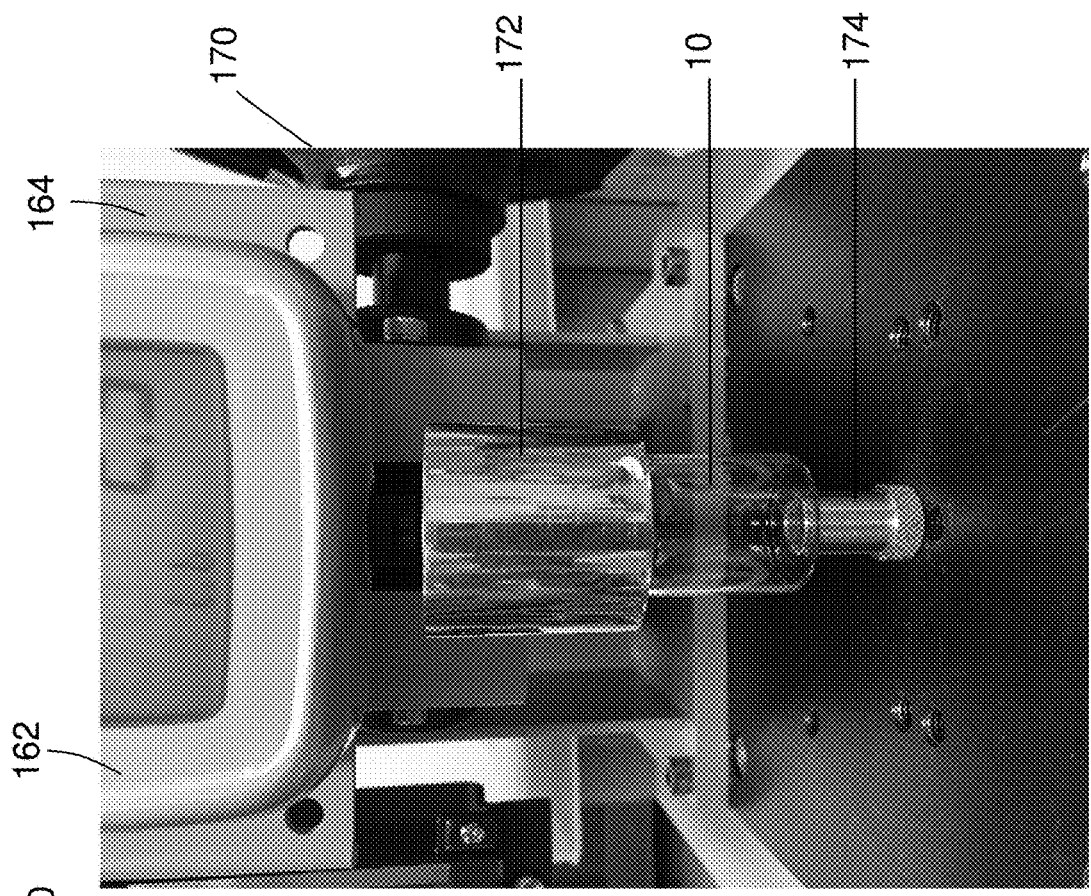
FIG. 8 is a front view of an apparatus configured to apply a force to the base or other portion of a vial.
Figure 9:
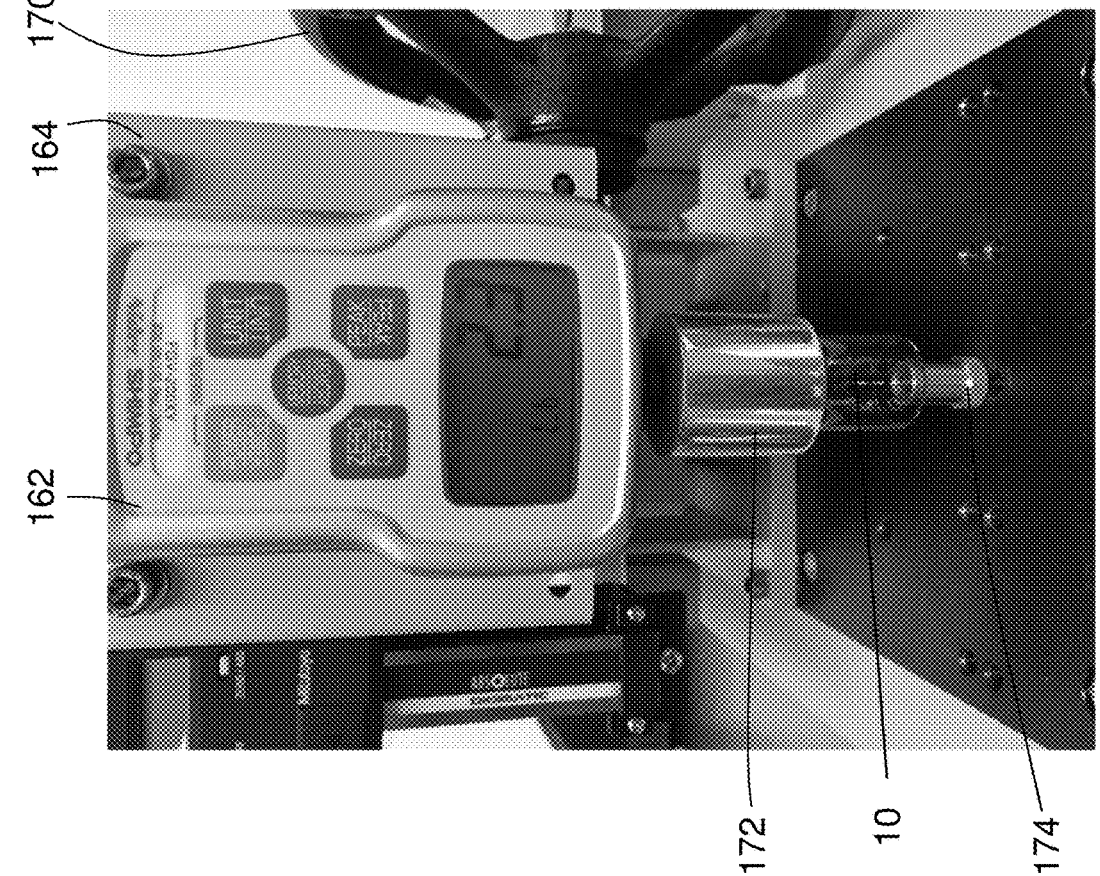
FIG. 9 is an enlarged view of FIG. 8.

Referring to FIGS. 8 and 9, after vial 10 has been scored as described above, a predetermined force may be applied to its base 26 to cause the surface defect to propagate across the heel glass. For some vials, this force is at least 2.3 pounds. For other vials, a force of 30 pounds is applied. In other embodiments, the force may be slowing increased until there is evidence that the surface defect has sufficiently propagated, such as an audible snap or popping sound. The same vertical press 164 and force gauge 162 used to score the vial may be used to apply the force to its base. However, the awl is removed from force gauge 162 and replaced with a mandrel 172 configured to evenly contact the top of vial 10. Also, fixture 168 shown in FIGS. 6 and 7 is replaced with a small diameter, tube-shaped pedestal 174. Pedestal 174 may be secured to the base of press 164 below mandrel 172. As previously discussed relative to FIG. 5, the smaller the diameter of pedestal 174, the larger the leverage that is placed on heel 28. In some embodiments, the diameter of pedestal 174 is about half the diameter of vial 10.

Figure 11:
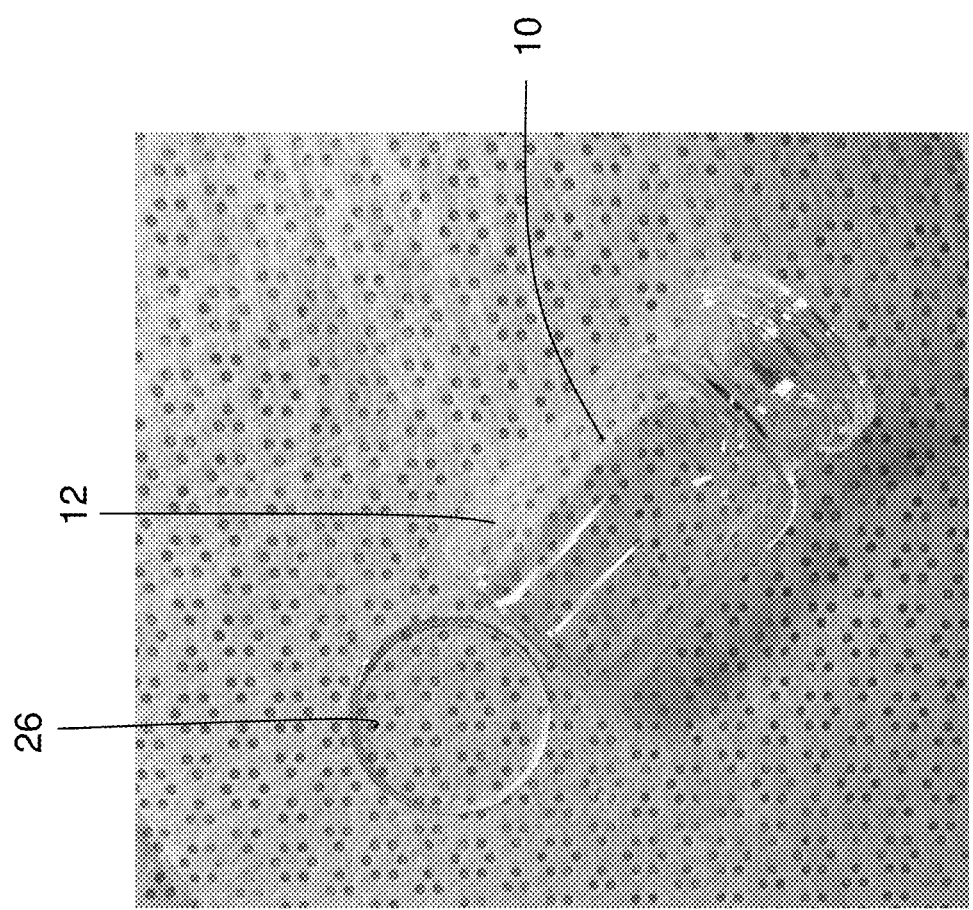
FIG. 11 is a plan view showing a lensed vial.
Figure 10:
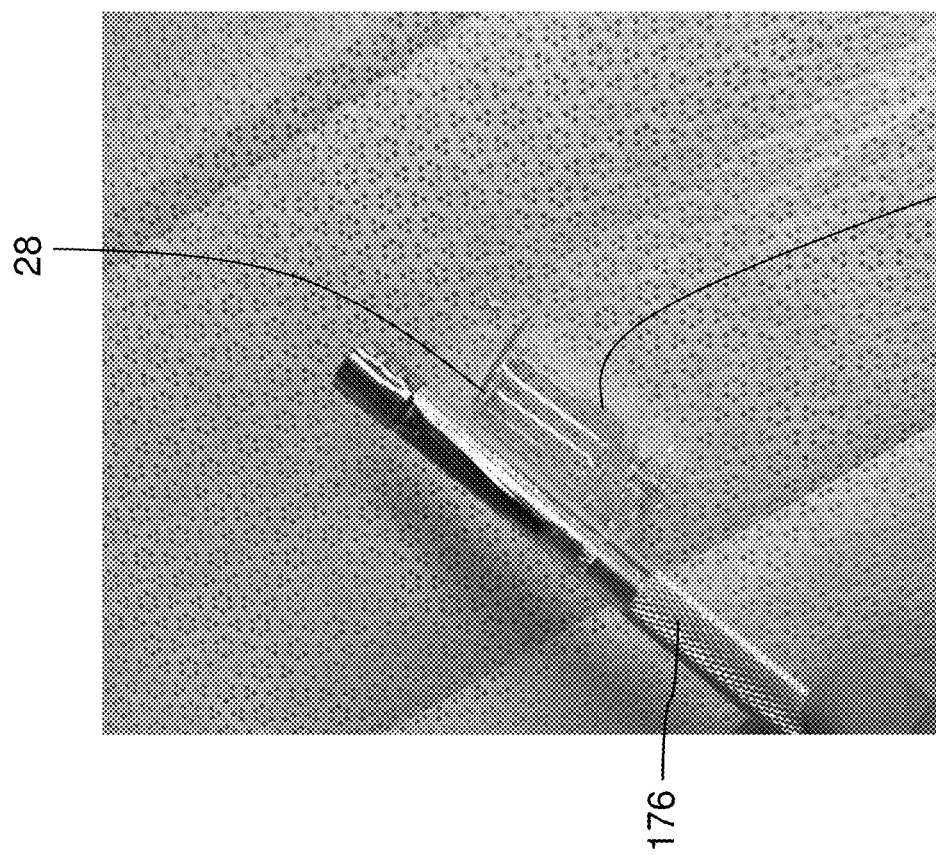
FIG. 10 is a plan view of a scored vial and a tool used to tap the fracture line.

Referring to FIG. 10, after vial 10 has been scored and/or a force applied to its base as described above, it may be wiped down to remove any contaminants that may have accumulated on it during the scoring process, such as glass particles or oil. A tool 176 may be used to gently tap on heel 28 to further break it away from the main body of vial 10. FIG. 11 shows vial 10 after it has been lensed (i.e. base 26 has been separated from main body 12.) While FIGS. 10 and 11 show an empty vial for clarity, in the actual inspection process vial 10 would still contain the lyo cake and the particle(s) of interest at this point.

Figure 12:
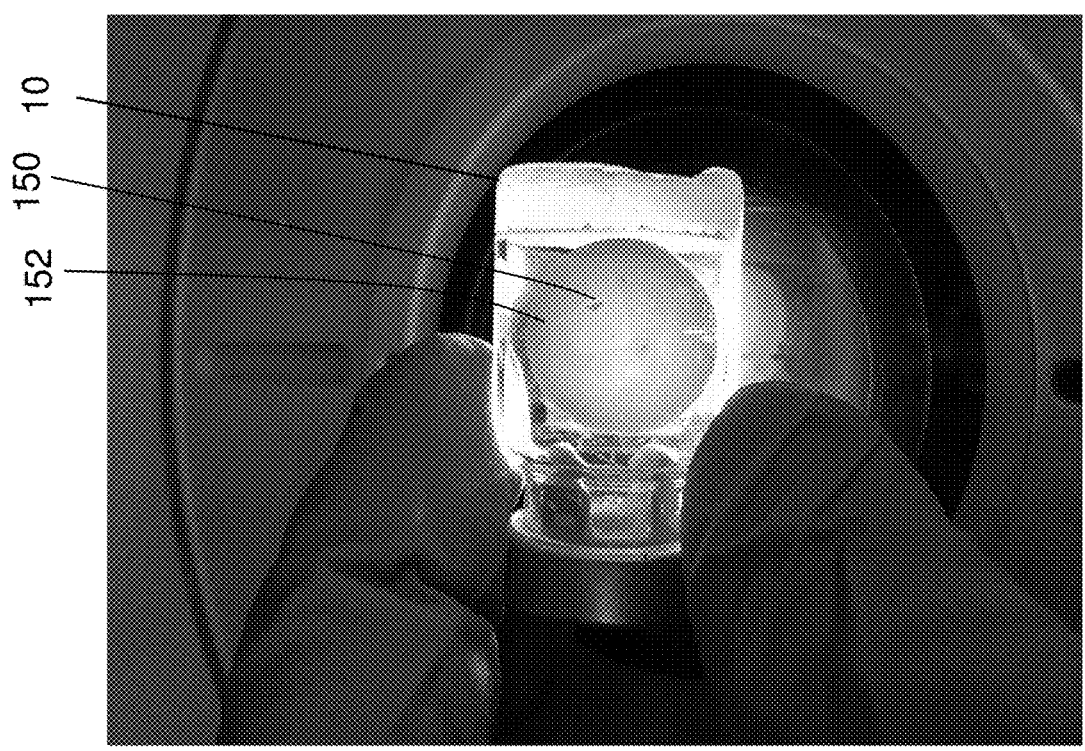
FIG. 12 is a side view showing a lensed vial whose contents are being illuminated.

Referring to FIGS. 12-15, step 130 of the exemplary inspection method 100, removing substantially the entire cake of lyophilized medicine through the enlarged opening of the lensed vial, will be described. Referring first to FIG. 12, lensed vial 10 may be placed on a light table again to confirm the occurrence of particle 150 a second time. The location of particle 150 on lyo cake 152 should be noted. Specifically, the distance from the center of the cake can be noted, as well as the clocking. Cake 152 can be manipulated to put particle 150 at a 3 o'clock or 12 o'clock position. This puts particle 150 on the analyzing equipment's horizontal or vertical axis which makes it easier to find when using the equipment.

Figure 13:
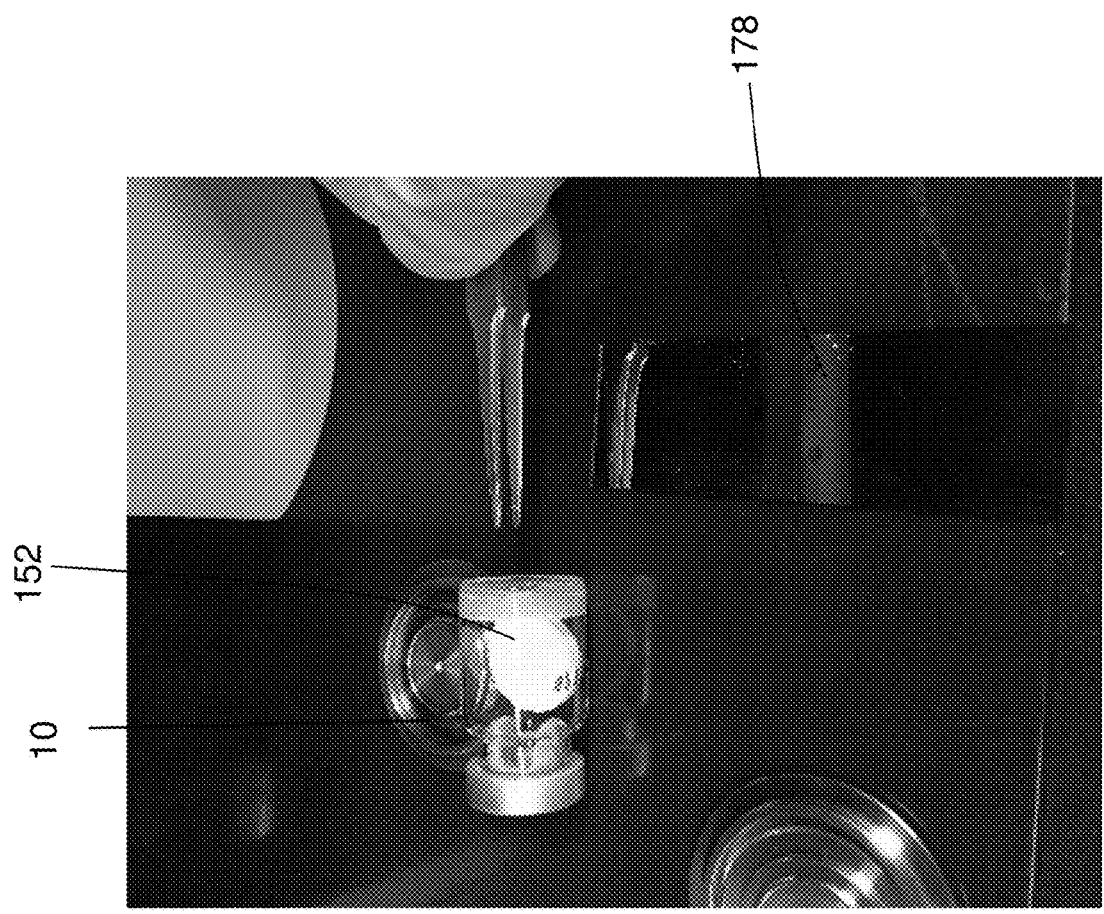
FIG. 13 is a perspective view showing the vial of FIG. 12 with its contents being removed.
Figure 15:
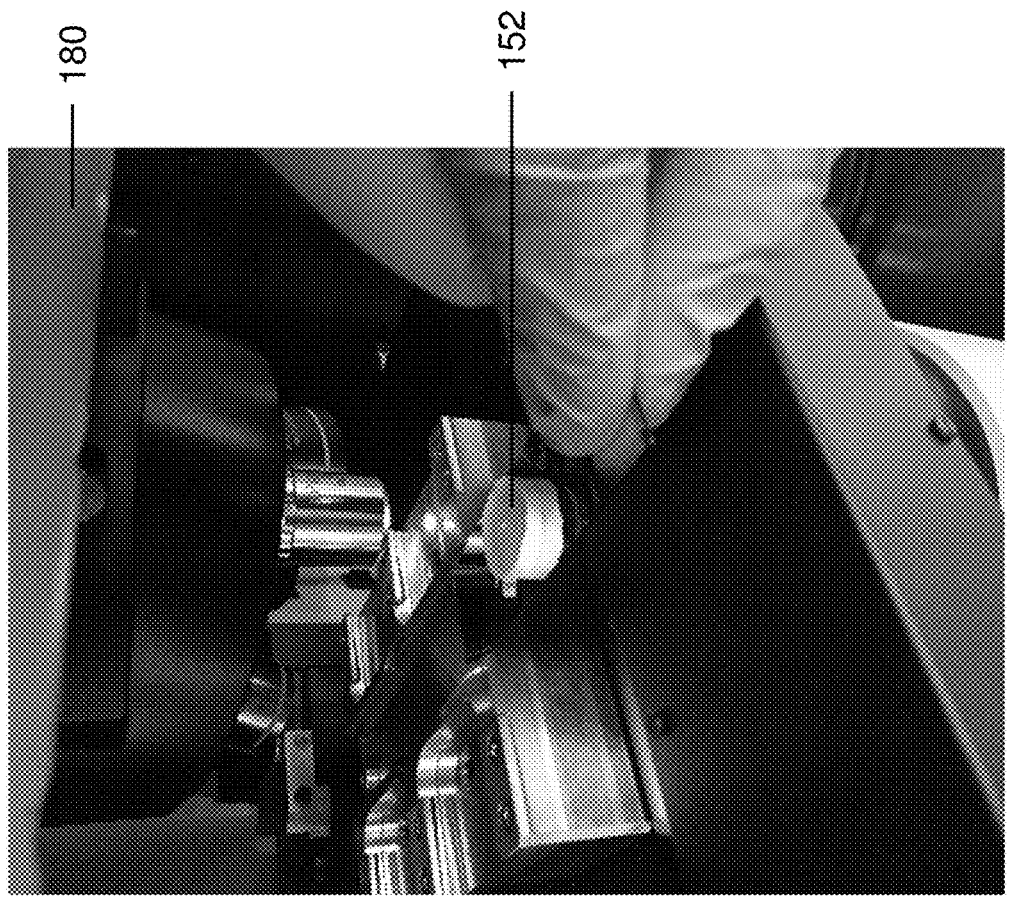
FIG. 15 is a perspective view showing the slide of FIG. 14 and its contents being placed in a LIBS system.
Figure 14:
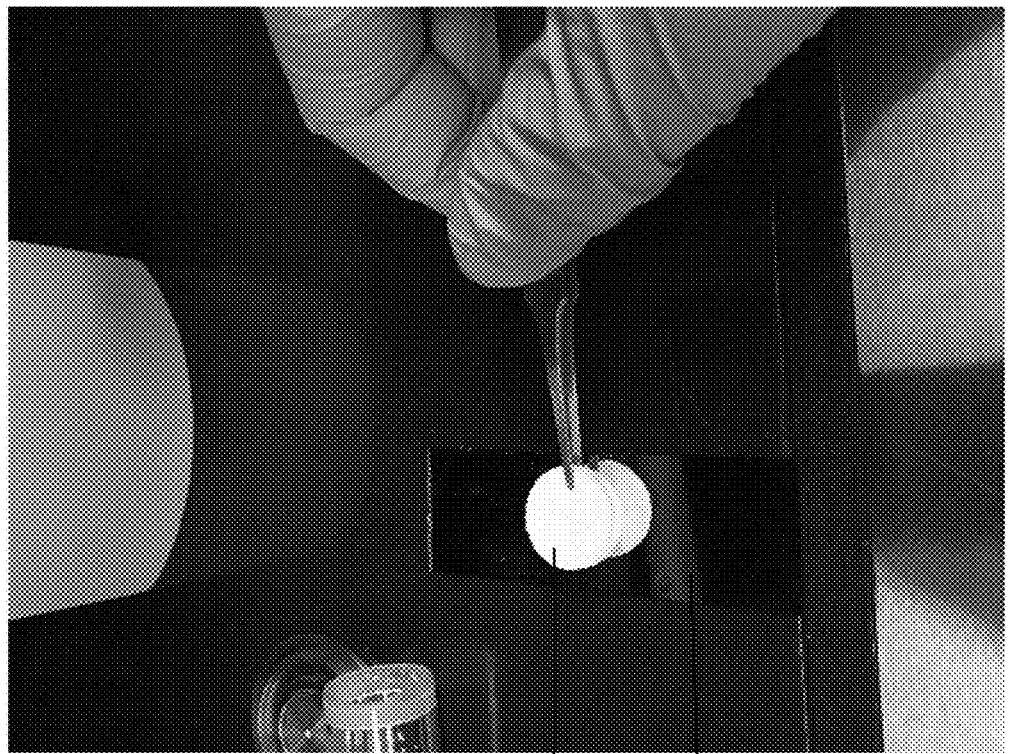
FIG. 14 is a perspective view showing the contents of the vial of FIG. 13 being transferred to a slide.
Figure 16:
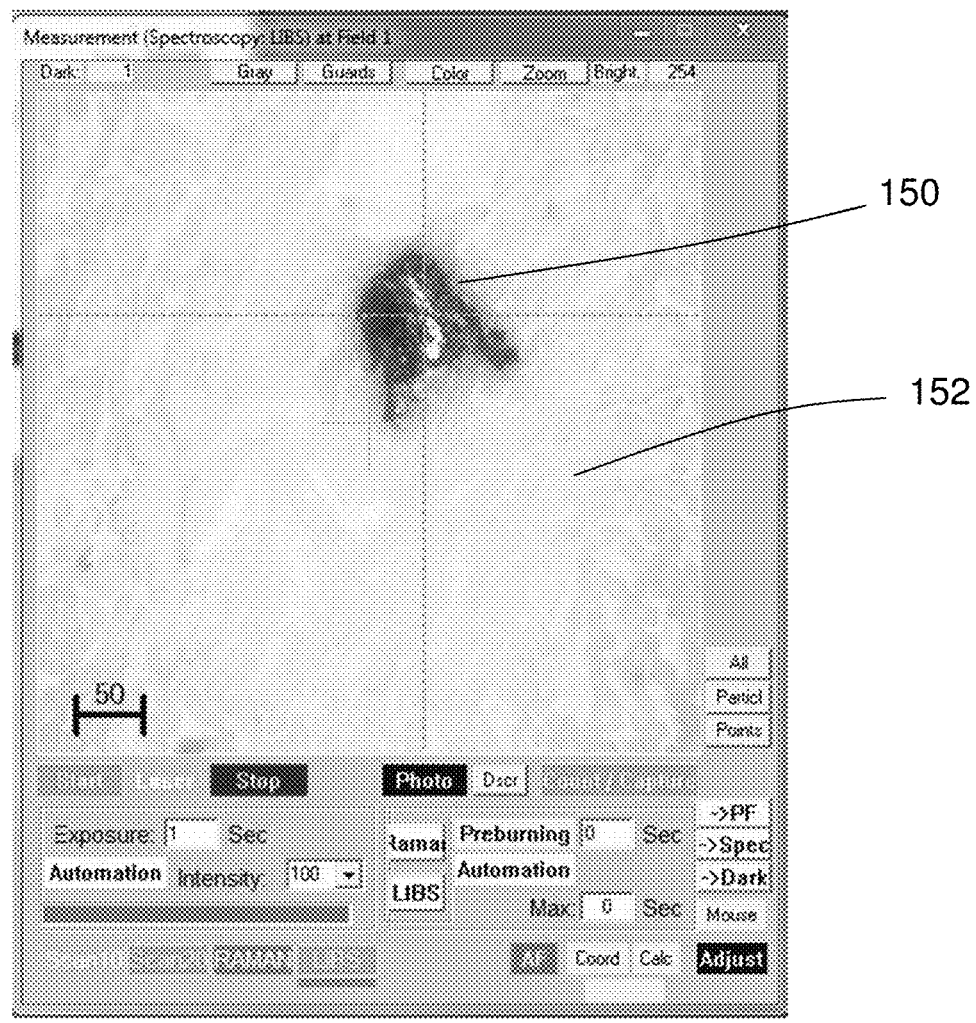
FIG. 16 shows a monitor screen of a LIBS system displaying a particle of interest.

As shown in FIGS. 13 and 14, tweezers may be used to gently transfer lyo cake 152 onto an appropriate fixture. In some embodiments, a gold plated glass slide 178 is used, even though cake 152 may be too thick to allow a laser to penetrate and create spectra from the slide. The clocked position and approximate location of particle 150 should again be noted. Slide 178 can then be placed in a spectrometer 180, as shown in FIG. 15. In some embodiments, particle 150 is then found using the vision system of spectrometer 180, as depicted in FIG. 16. In this third confirmation of particle 150, its morphology should be analyzed. In some embodiments, if the morphology is consistent with previous images, and with other particles that were previously identified as stainless steel, the inspection personnel should continue with the atomic emissions spectroscopy (AES) technique, such as laser-induced breakdown spectroscopy (LIBS) analysis. In some embodiments, Raman spectroscopy can be performed at this point. However, if particle 150 is metal, it likely will not give a good signal and the Raman spectroscopy could heat the metal and cause the speck to sink into the cake 152.

Referring to FIGS. 17-20, step 140 of the exemplary inspection method 100, analyzing the contaminant using an atomic emissions spectroscopy (AES) technique, will be described. In this exemplary embodiment, laser-induced breakdown spectroscopy (LIBS) analysis is the AES technique used. In some embodiments, the sample particle is not touched at all as the lyo cake with the particle on it is removed from the vial it was found in and placed in the LIBS equipment. The entire analysis may be performed with the sample particle remaining undisturbed on the lyo cake.

In some embodiments, the LIBS equipment operates by focusing a laser (typically a Nd:YAG solid-state laser) onto a small area at the surface of the specimen. When the laser is discharged it ablates a very small amount of material, in the range of nanograms to picograms, which generates a plasma plume with temperatures in excess of 100,000 K. During data collection, typically after local thermodynamic equilibrium is established, plasma temperatures range from 5,000-20,000 K. At the high temperatures during the early plasma, the ablated material dissociates (breaks down) into excited ionic and atomic species. During this time, the plasma emits a continuum of radiation which does not contain any useful information about the species present, but within a very small timeframe the plasma expands at supersonic velocities and cools. At this point the characteristic atomic emission lines of the elements can be observed. The delay between the emission of continuum radiation and characteristic radiation is in the order of 10 µs, which is why the detector is typically temporally gated.

In step 140 of the exemplary inspection method 100, the atomic emission lines generated by the particle being studied with the LIBS equipment are compared to emission lines in a library of reference samples. In some embodiments, the library contains not only spectra from standard elements, but also reference samples created from particles found in pharmaceutical processing equipment. For example, particles may be sampled from specific parts of pharmaceutical manufacturing equipment, vial filling equipment, etc. with each being cataloged as to its source. When the spectra of a particle being analyzed matches the spectra of a library reference, the source of the vial contamination may then be quickly determined and remedied.

Figure 17:
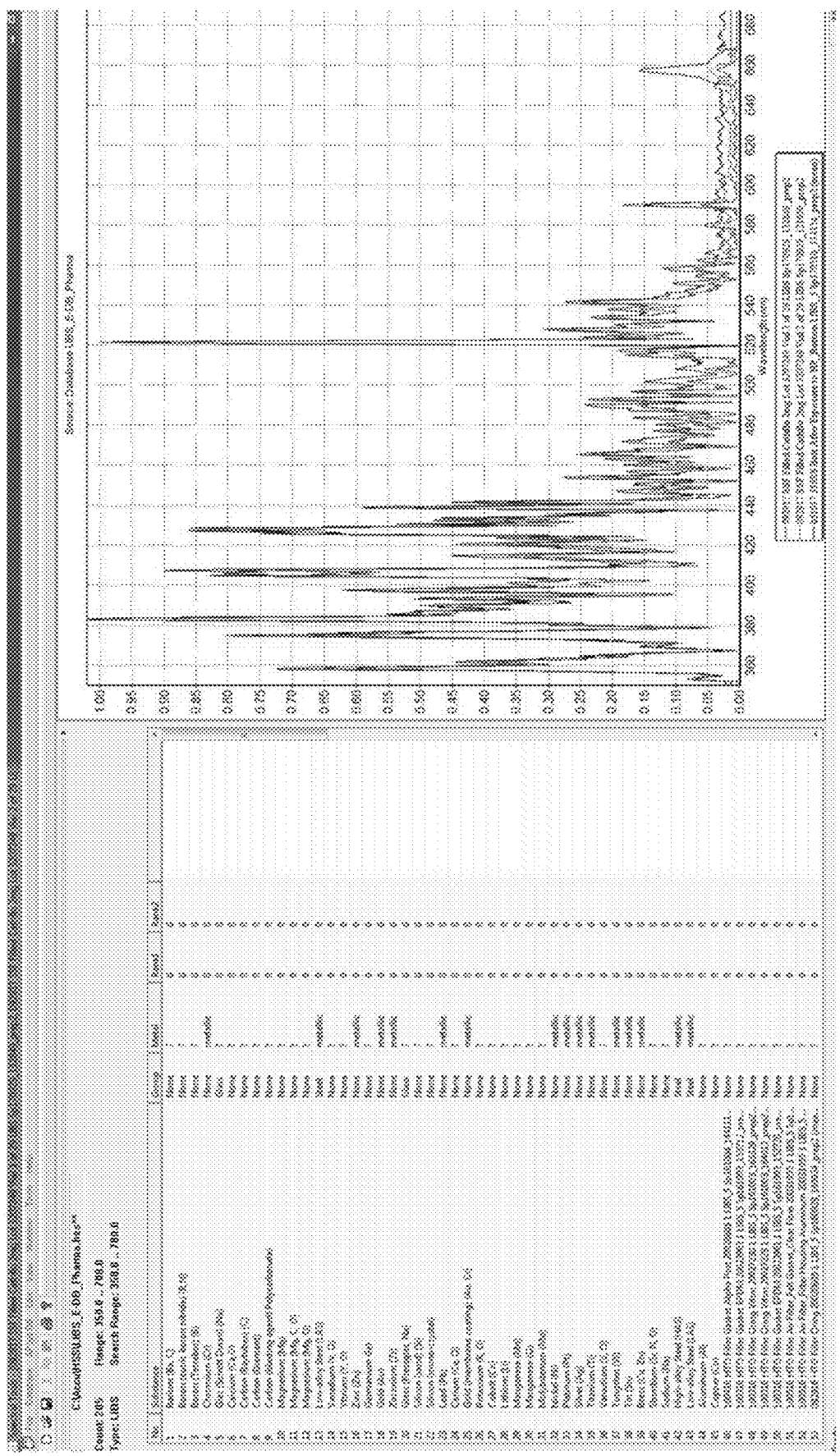
FIG. 17 shows a monitor screen of a LIBS system displaying the signal from a particle of interest with a normalized amplitude.

Referring first to FIG. 17, an example of two LIBS sample spectra being compared to a library reference spectra is provided on the right side of the figure. On the left side of the figure, an example listing of library references is shown. In some embodiments, the LIBS equipment provides a ranking of how close a match there is between the sample and the library references.

In some embodiments, the spectra of the lyo cake may essentially be moot for the LIBS analysis when compared to non-organic material. However, it may still be important to look at the actual spectra themselves and not just the library matches. This is because the library references may be normalized in some embodiments. The discussion below related to FIGS. 18 and 19 amplifies this point.

Figure 18:
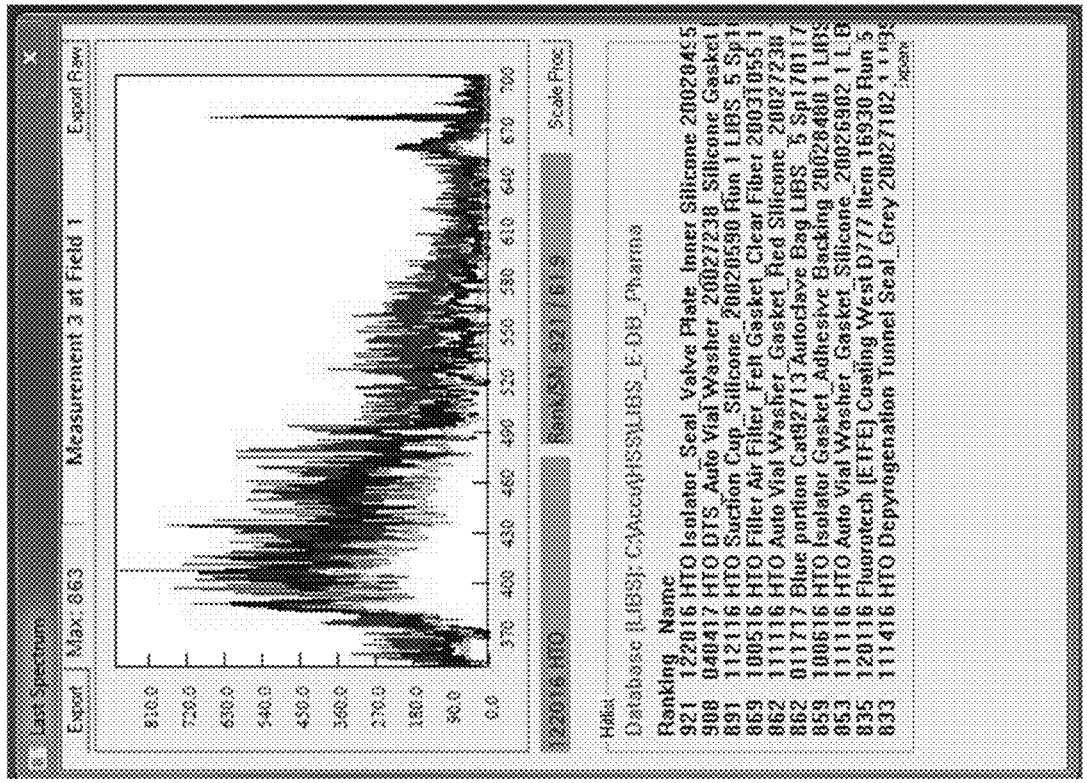
FIG. 18 shows a monitor screen of a LIBS system displaying the signal from a stainless steel particle with a non-normalized amplitude.

Referring to FIG. 18, an example of a LIBS analysis of a stainless steel particle sample is provided. In this example, the amplitude of the signal is high. The raw signal is processed/normalized and compared to the reference library, resulting in a strong signal.

Figure 19:
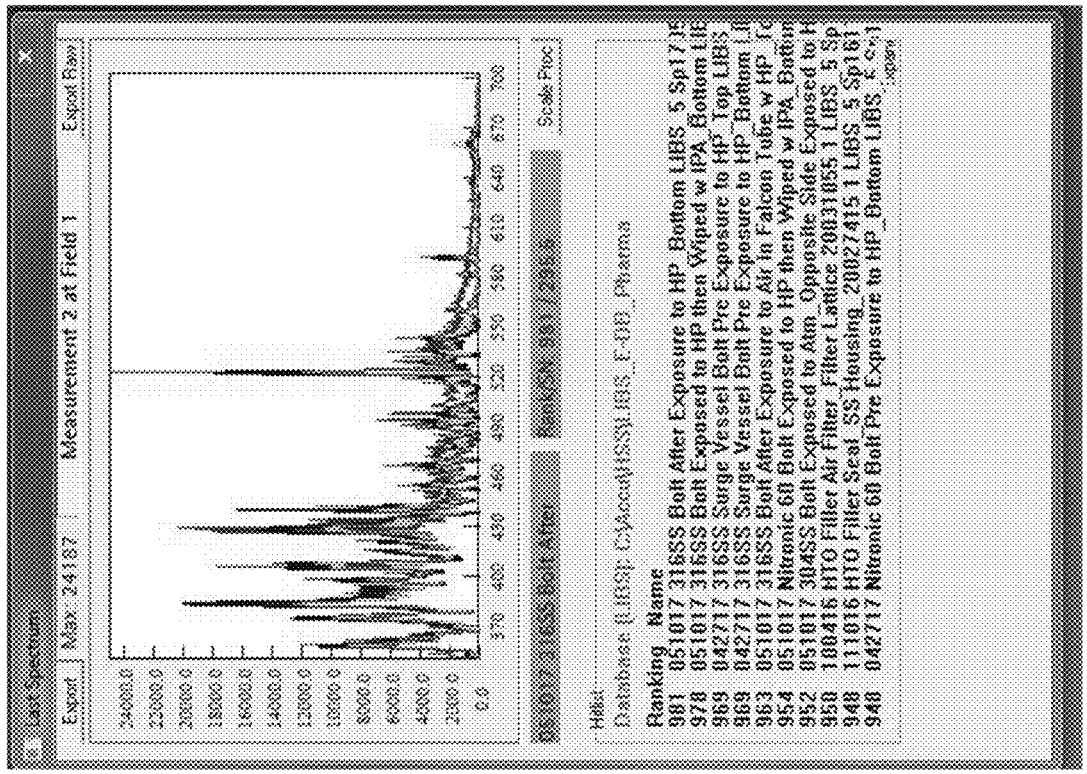
FIG. 19 shows a monitor screen of a LIBS system displaying the signal from a lyo cake with a non-normalized amplitude.
Figure 20:
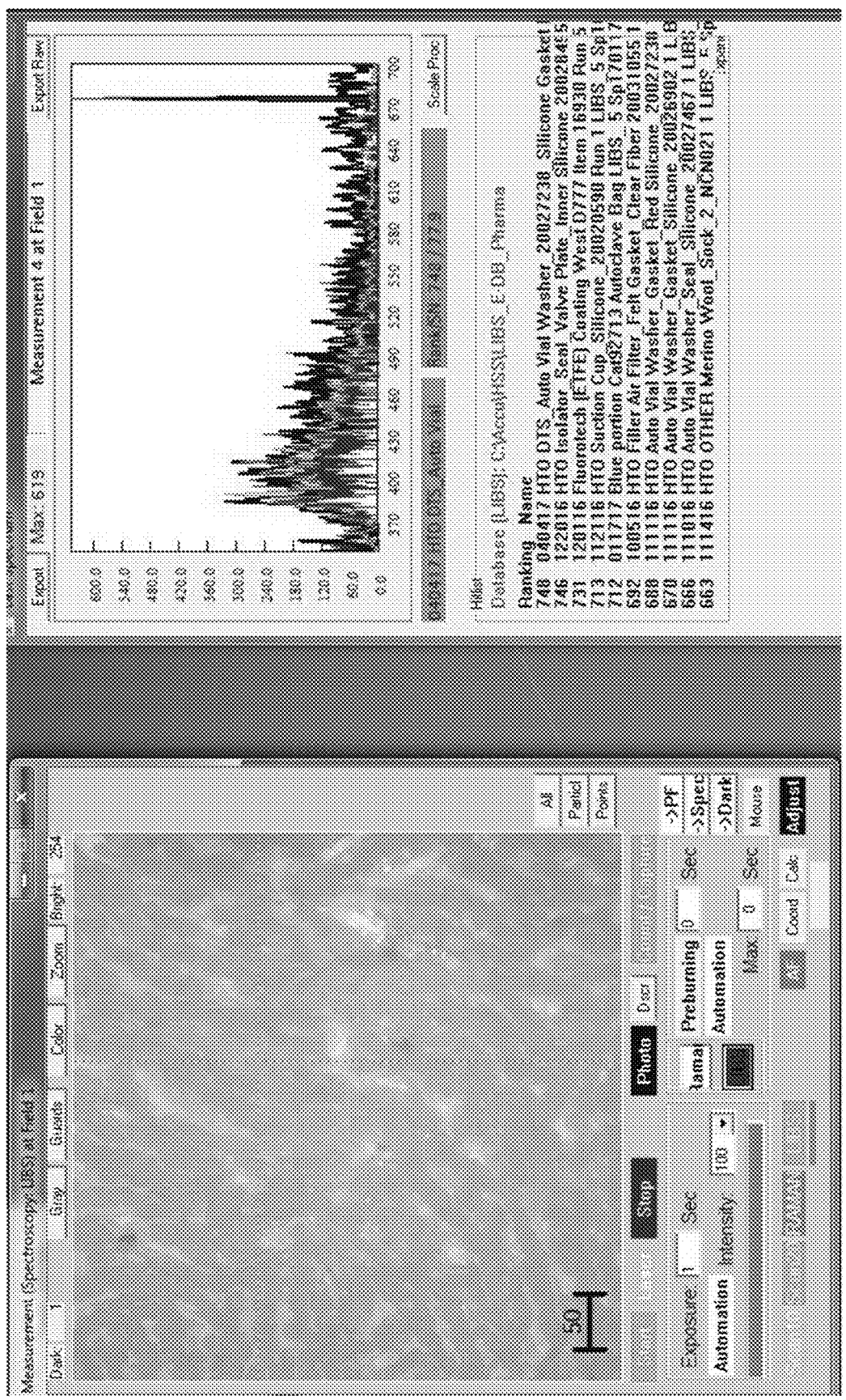
FIG. 20 shows a monitor screen of a LIBS system displaying the signal and an image from a lyo cake.

Referring to FIG. 19, an example of a LIBS analysis of the lyo cake itself is provided. Here, the signal amplitude is low, but the signal to noise ratio is acceptable. In this example, the LIBS equipment is showing a high match with a silicon sample from its library. This false match occurs here because the low amplitude of the lyo cake signal has been increased/normalized, and because the lyo cake signal is dirty/noisy. In particular, both the sample signal and the library signal will be scaled from 0 to 1 when normalized, when in reality one may have an actual amplitude much higher than the other. Comparing FIG. 18 (stainless steel particle) to FIG. 19 (lyo cake), the signals appear to have similar amplitudes, but the stainless steel signal has an actual amplitude that is much higher than that of the lyo cake. Therefore, when using LIBS to analyze a sample particle resting on a lyo cake, attention should be paid to the amplitude of the signal. If the target of the LIBS equipment is off, the cake could be analyzed instead of the particle, as depicted in FIG. 20.

Figure 21:
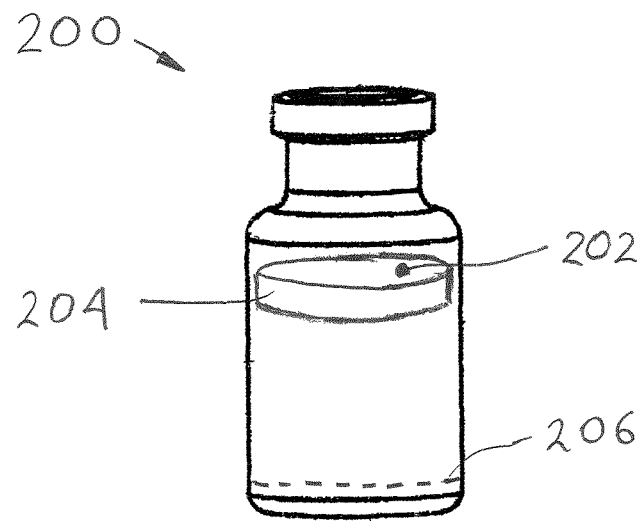
FIG. 21 is a side view showing a molded vial being opened near its base.
Figure 22:
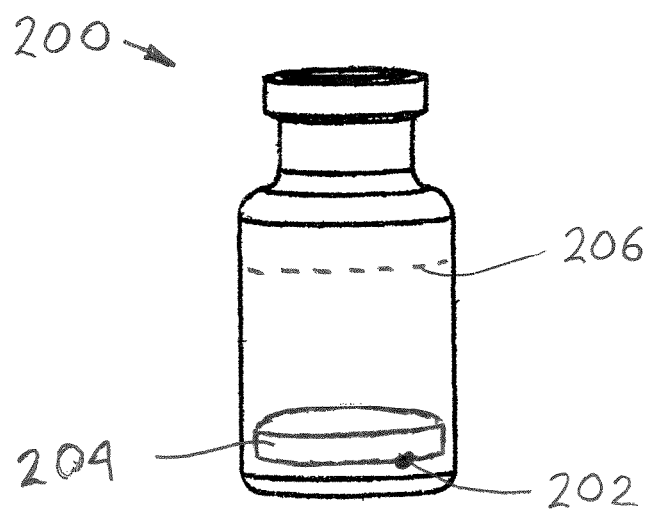
FIG. 22 is a side view showing a molded vial being opened near its collar.

Referring to FIGS. 21 and 22, an alternative method for lensing or detaching a base of a vial is provided. Glass vials for use in the medicine industry are often either a "tubing vial" or a "molded vial." The manufacture of tubing vials is typically performed by converting a glass cane (tube) into a vial through the use of flames, tools and rotation of the cane/tube to close the bottom of the vial and form the features at the top of the vial. In contrast to tubing vials, molded vials are typically manufactured using a "glob" of molten glass that is inserted into a die and then expanded using compressed air to take the same shape as the inside of the die. Because of the way tubing vials are manufactured, their dimensions tend to be very consistent, with only small variances in the glass wall thickness. Repeatable results can therefore be anticipated when lensing tubing vials. The dimensions of molded vials on the other hand tend to be consistent only where their outer portions mate with the die. However, there is typically a large variance in the wall thickness throughout the vial. These glass wall thickness variations in molded vials can cause less predictable results during the lensing of the base using the previously described procedure above. Accordingly, the procedure described above in reference to FIGS. 2-11 is best suited for tubing vials, and the procedure described below with reference to FIGS. 21 and 22 is best suited for molded vials. However, either procedure may be used for either type of vial.

To allow access to the lyophilized cake in a molded glass vial 200 for spectral analysis, the base may be removed by first cutting a pattern partially through the wall thickness around the entire circumference of the vial, and then placing the pattern in tension to break the uncut portion of the wall thickness. Due to the difference in molded vial glass wall thickness, care should be taken to prevent cutting into the interior of the vial, as that could introduce contamination. In some implementations, a band saw adapted for cutting glass is used to create a controlled cut around the circumference of the vial in the desired location. If the particle 202 to be analyzed is in the top of the lyophilized cake 204 as depicted in FIG. 21, then it is recommended to first shift the cake 204 toward the top of vial 200 and then make the cutting pattern 206 near the base of vial 200 as shown. Cutting vial 200 on the opposite side of cake 204 from particle 202 minimizes the chance of introducing contamination onto the lyophilized cake. On the other hand, if the particle 202 is on the bottom of the cake 204 as depicted in FIG. 22, it may be desirable to cut the pattern 206 near the shoulder of the vial as shown.

Once the cut pattern 206 is made around the circumference of molded vial 200 as described above, appropriate personal protective equipment should be donned before inserting a flat-bladed screwdriver or other suitable tool into the cut 206 and twisting the tool in a controlled manner, thereby placing the glass in tension. It is expected that the fracture will follow the path of least resistance/strength and thus along the cut pattern 206, but due to the variations in molded vial glass wall thickness, the fracture may take another direction. The overall intent is to allow removal of the cake for analysis of the particle; a clean fracture is preferred but not necessary for the removal of the cake.

Advantages provided by the vial contents inspection and identification method 100 described herein and variations thereof include the following. The method can ensure that the analysis is being performed on only the particle that was identified during culling and is a conclusive method. Prior art methods of analyzing particulate matter in lyophilized vial contents involve reconstituting the vial contents by adding Water for Injection (WFI), removing the reconstituted contents from the vial, and isolating the particulate matter by filtering. This typically involves multiple rinses of the vial and filtering equipment and can take one to two hours per vial. The present exemplary method reduces the chance of contamination during reconstitution, such as by rubber from a stopper, glass from interaction with the seal during crimping, stainless steel from the syringe, aluminum from the seal, and/or anything that is inherent to the filtering process. The method also reduces the time required for filtration from 1-2 hours down to 6-10 minutes, and reduces/eliminates the cost of filtration. The method also allows for multiple analyses to be conducted on the particle of interest. While LIES can be considered a 'destructive' test, in many instances the particle is merely 'liberated' from a filter by a LIBS laser, not completely destroyed. Additionally, in some tests there may be something hidden in the lyo cake. Using LIBS to analyze just the particle of interest on top of the lyo cake as disclosed herein prevents such hidden elements from interfering with the analysis.

In some implementations of the inspection and identification method, after the lyo cake is removed from the vial, a smaller portion of the cake is isolated and analyzed using LIBS and/or with traditional reconstitution methods. In some implementations, the particle may be directly picked from the cake after it is removed from the vial but before it is analyzed.

What is claimed is:

1. A method of inspecting and performing material identification of a contaminant found in a vial containing a cake of lyophilized medicine, the method comprising:
   identifying the presence of a contaminant in the lyophilized medicine;
   detaching a portion of the vial to create an enlarged opening in the vial;
   removing substantially an entire cake of lyophilized medicine through the enlarged opening; and
   analyzing the contaminant while it remains on the removed cake of lyophilized medicine using an atomic emissions spectroscopy (AES) technique.

2. The method of claim 1, wherein the AES technique comprises laser-induced breakdown spectroscopy (LIBS).

3. The method of claim 1, wherein the contaminant is a speck.

4. The method of claim 3, wherein the speck comprises stainless steel.

5. The method of claim 1, wherein the step of detaching the portion of the vial comprises scoring a heel of the vial.

6. The method of claim 5, wherein a fixture is used to position the vial relative to an awl.

7. The method of claim 6, wherein the fixture allows the vial to be rotated relative to the awl.

8. The method of claim 6, wherein the vial has a central longitudinal axis and wherein the fixture holds the vial such that its axis is at a non-perpendicular angle relative to the awl.

9. The method of claim 8, wherein the non-perpendicular angle is about 75 degrees.

10. The method of claim 1, wherein the step of detaching the portion of the vial comprises applying a force to a base of the vial at a diameter that is smaller than a diameter of the base.

11. The method of claim 10, wherein the force is applied to the base at a diameter that is about half of the diameter of the base.

12. The method of claim 10, wherein a force gauge is used to measure the force being applied to the base.

13. The method of claim 12, wherein the force gauge is mounted on a press configured to move the force gauge relative to the vial.

14. The method of claim 1, wherein the step of detaching the portion of the vial comprises tapping a heel of the vial.

15. The method of claim 1, further comprising confirming the occurrence of the contaminant at least three times.

16. The method of claim 1, wherein the step of analyzing the contaminant comprises comparing a signal associated with the contaminant with a signal associated with a sample taken from a component of pharmaceutical processing equipment.

17. The method of claim 16, wherein the contaminant signal is compared to a library comprising at least ten samples taken from different components of pharmaceutical processing equipment.

18. The method of claim 1, wherein the vial is a tubing vial and the base of the vial is detached.

19. The method of claim 1, wherein the vial is a molded vial and either the base or an upper portion of the vial is detached.

20. The method of claim 1, wherein the step of identifying the presence of a contaminant in the lyophilized medicine comprises visibly identifying the contaminant on the lyophilized medicine in the vial before the lyophilized medicine is removed from the vial for testing.

21. The method of claim 1, wherein the cake of lyophilized medicine is not altered before the analyzing step.

22. A method of inspecting and performing material identification of a contaminant found in a vial containing a cake of lyophilized medicine, the method comprising:
- identifying the presence of a contaminant speck in the lyophilized medicine;
- positioning the vial relative to an awl using a fixture, wherein the fixture holds the vial such that a longitudinal axis of the vial is at a non-perpendicular angle relative to the awl;
- contacting a heel of the vial with the awl;
- rotating the vial relative to the awl using the fixture, thereby scoring the heel of the vial with the awl;
- detaching a portion of the vial to create an enlarged opening in the vial;
- removing substantially an entire cake of lyophilized medicine through the enlarged opening; and
- analyzing the contaminant while it remains on the removed cake of lyophilized medicine using laser-induced breakdown spectroscopy (LIBS).

\* \* \* \* \*